(12) United States Patent
Zhou et al.

(10) Patent No.: US 8,133,274 B2
(45) Date of Patent: Mar. 13, 2012

(54) PHOTOCHROMIC INTRAOCULAR LENSES AND METHODS OF MAKING THE SAME

(75) Inventors: Stephen Q. Zhou, Irvine, CA (US); Christopher D. Wilcox, Mission Viejo, CA (US); Christine J. Liau, Irvine, CA (US)

(73) Assignee: Medennium, Inc., Irvine, CA (US)

( * ) Notice: Subject to any disclaimer, the term of this patent is extended or adjusted under 35 U.S.C. 154(b) by 1609 days.

(21) Appl. No.: 11/150,982

(22) Filed: Jun. 13, 2005

(65) Prior Publication Data

US 2005/0283234 A1    Dec. 22, 2005

Related U.S. Application Data

(60) Provisional application No. 60/580,852, filed on Jun. 18, 2004.

(51) Int. Cl.
*A61F 2/16* (2006.01)
(52) U.S. Cl. .................... 623/6.56; 623/6.6
(58) Field of Classification Search ........ 623/6.18–6.21, 623/6.56–6.6
See application file for complete search history.

(56) References Cited

U.S. PATENT DOCUMENTS

| | | | |
|---|---|---|---|
| 4,731,079 A * | 3/1988 | Stoy ............................ | 623/6.58 |
| 4,871,363 A | 10/1989 | Kelman | |
| 5,074,942 A * | 12/1991 | Kearns et al. ................ | 156/154 |
| 5,112,883 A * | 5/1992 | Gallas ........................... | 523/106 |
| 5,166,345 A * | 11/1992 | Akashi et al. ................... | 544/71 |
| 5,444,106 A | 8/1995 | Zhou et al. | |
| 5,662,707 A | 9/1997 | Jinkerson et al. | |
| 6,113,814 A | 9/2000 | Gemert et al. | |
| 6,224,210 B1 | 5/2001 | Chateau et al. | |
| 6,224,945 B1 | 5/2001 | Calderara | |
| 6,271,281 B1 | 8/2001 | Liao et al. | |
| 6,432,137 B1 | 8/2002 | Nanushyan et al. | |
| 6,465,588 B1 * | 10/2002 | Li ................................. | 526/258 |
| 6,673,886 B2 * | 1/2004 | Vanderbilt .................. | 526/319 |
| 6,679,605 B2 | 1/2004 | Zhou et al. | |
| 6,780,899 B2 | 8/2004 | Liao et al. | |
| 6,896,926 B2 * | 5/2005 | Qiu et al. ..................... | 427/2.31 |
| 6,926,965 B2 * | 8/2005 | Qiu et al. ..................... | 428/411.1 |
| 7,241,312 B2 * | 7/2007 | Lai et al. ....................... | 623/6.62 |
| 7,297,725 B2 * | 11/2007 | Winterton et al. ............ | 523/107 |
| 2002/0082691 A1 | 6/2002 | Christ et al. | |
| 2002/0182316 A1 * | 12/2002 | Gilliard et al. ............... | 427/162 |
| 2003/0008958 A1 * | 1/2003 | Momoda et al. ............. | 524/368 |
| 2003/0065051 A1 * | 4/2003 | Winterton et al. ............ | 523/106 |
| 2003/0078359 A1 * | 4/2003 | Ichinohe ........................ | 528/25 |
| 2003/0164481 A1 * | 9/2003 | Havens et al. ................ | 252/582 |
| 2004/0041289 A1 * | 3/2004 | Ichikawa et al. ............. | 264/1.32 |
| 2004/0056371 A1 | 3/2004 | Liao et al. | |
| 2004/0185268 A1 * | 9/2004 | Kumar et al. ................ | 428/446 |
| 2004/0186241 A1 | 9/2004 | Gemert | |
| 2005/0055091 A1 * | 3/2005 | Lai et al. ...................... | 623/5.16 |
| 2005/0254003 A1 | 11/2005 | Jani et al. | |
| 2007/0197750 A1 | 8/2007 | Gibanel et al. | |
| 2008/0200983 A1 | 8/2008 | Bernard et al. | |

FOREIGN PATENT DOCUMENTS

| | | |
|---|---|---|
| WO | WO 9811848 A1 | 3/1998 |
| WO | WO 9853744 A1 | 12/1998 |
| WO | WO 0057213 A1 | 9/2000 |

OTHER PUBLICATIONS

Sparrow, J. et al., Blue light-absorbing intraocular lens and retinal pigment epithelium protection in vitro, J Cataract Refract Surg. 2004; 30:873-878.
Alcon Laboratories, Inc., Acrysof® Natural Single-Piece IOL Product Monograph, Alcon, Inc. Fort Worth, Texas, USA, 2004.
www.cataractsurgery.com/us/professional/natural/default.asp, About the ACRYSOF® Natural IOL, ACRYSOF® product information, Alcon, Inc. 2005. Printed Aug. 3, 2005.
Zack, P., et al., UV-blue-light-absorbing photochromic intraocular lens for protection against age-related macular degeneration development, Proceedings of SPIE, pp. 102-104, vol. 2579, Oct. 1998.
Mester et al, Intraindividual Comparison of a Blue-Light Filter on Visual Function: AF-1 (UY) Versus AF-1 (UV) Intraocular Lens J. Cataract Refr. Surg. 34: 608-615 (2008).
Kolozsvari et al, UV Absorbance of the Human Cornea in the 240- to 400-NM Range Investigative Ophthalmology and Visual Sciences, 43: 2165-2168 (2002).
Werner at al, New Photochromic Foldable Intraocular Lens: Preliminary Study of Feasibility and Biocompatibility Journal Cataract Infracted Surgery (32: 1214-1221 (2006)).

* cited by examiner

*Primary Examiner* — David H Willse
*Assistant Examiner* — Tiffany Shipmon
(74) *Attorney, Agent, or Firm* — Steven J. Goldstein; Frost Brown Todd, LLC

(57) ABSTRACT

Intraocular lenses containing a photochromic agent, are disclosed. Specifically, the foldable intraocular lens of the present invention comprises an optic body made from a crosslinked material comprising at least one monomer, a crosslinker, a UV absorber, and a photochromic agent which has a maximum absorption peak of about 400-500 nm in its excited state. The lens has a glass transition temperature of about 37° C. or lower. Methods for making these intraocular lenses are also taught.

19 Claims, No Drawings

PHOTOCHROMIC INTRAOCULAR LENSES AND METHODS OF MAKING THE SAME

CROSS-REFERENCE TO RELATED APPLICATION

This application is based upon and claims priority from U.S. Provisional Application No. 60/580,852, Zhou et al., filed Jun. 18, 2004, incorporated herein by reference.

BACKGROUND OF THE INVENTION

Intraocular lenses (IOLs) have been widely used after patients undergo surgical cataract removal. In 2003, there were approximately 15 million IOLs sold worldwide, including 2.5 million in the US. The standard IOL today is made from biocompatible foldable polymers containing a UV absorber. Such an IOL can filter out UV A (200-315 nm wavelength) and UV B (315-380 nm wavelength) effectively to provide sufficient protection for the patient as far as UV light damage is concerned.

In recent years, there have been some concerns about potential blue light damage to the retina. For this reason, Alcon Laboratories, Inc. introduced ACRYSOF® Natural into the U.S. market in 2003. ACRYSOF® Natural is a foldable IOL made from a hydrophobic acrylic copolymer containing both a UV absorber and a blue light absorber. It not only absorbs UV light but also blue light. The theoretical basis for ACRYSOF® Natural is that blue light (400 nm to 470 nm) has been demonstrated to cause damage to retinal pigment epithelial cells in vitro, as well as in some animal studies. Since age-related macular degeneration is caused by the degeneration of the retinal pigment epithelial cells, blocking blue light from reaching the retina, such as by blue light absorbing IOLs, might reduce the risk for or progression of age-related macular degeneration. Nevertheless, the clinical implications of these theoretical analyses have not yet been determined.

The blue light-absorbing IOL has a yellow tint due to its absorption of blue light. In addition to the potential protective effect for the retina, the absorption of the short wavelength visible light (blue light) can enhance contrast when viewing bright objects against a blue-based background, such as the sky (see Janet R. Sparrow, et al, "Blue light-absorbing intraocular lens and retinal pigment epithelium protection in vitro", J. Cataract Refract. Surg. 2004, 30:873-878). On the other hand, the yellow tint can compromise a patient's color perception, especially in a weak light environment, such as driving at night. Proponents suggest that the yellow tinted color provides senior patients, whose natural crystalline lens has become increasingly yellow due to aging, with natural color perception after their cataract lens is removed and replaced with the IOL. Critics argue that while it could be true that blue light absorbing IOLs may provide a patient with a natural view in a strong light environment, the decrease in color perception may compromise a patient's capability to drive at night and under other low light conditions. Accordingly, an ideal IOL would have a yellow color and absorb blue light in a strong light environment, such as an outdoor environment under a sunny sky, while under weak light conditions, such as indoors, the IOL would become colorless so that the patient could return to normal color perception. The goal of the present invention is precisely to provide such an ideal IOL for patients.

Photochromic spectacles have been widely used in the last decade. A photochromic spectacle darkens when exposed to UV light in an outdoor environment. When in an environment where there is no UV light, photochromic spectacles change back into a colorless state. Photochromic contact lenses have also been reported in the literature. U.S. Pat. No. 6,224,945, Calderara, issued May 1, 2001, discloses a process for manufacturing a crosslinked transparent hydrophilic polymer with photochromic dyes by impregnating the polymer material with a photochromic agent in an organic solvent and then rinsing the polymer with an aqueous solution. Calderara applied his invention to contact lenses. Those who are skilled in the art will understand that hydrophobic polymers, such as those used in IOLs, would typically not be appropriate for use in Calderara's method.

To our best knowledge, there has been no report of photochromic IOLs, particularly photochromic IOLs with blue light absorption in their activated state. There could be a number of good reasons why photochromic IOLs have not been explored. First, IOLs in the marketplace generally provide sufficient UV protection for both UV A and UV B, while the photochromic dye usually is used to lower the light transmittance of UV light and/or selected visible light range; the benefit for using a photochromic agent in an IOL is, therefore, not obvious. Second, there is a possibility that a photochromic agent may not change color inside the eye because there may not be sufficient UV light rays entering the eye through the cornea to activate the dye. The cornea is the first layer of protection to prevent hazardous UV light rays from entering the eyes and damaging the natural lens and retina. In spite of this uncertainty, the present invention has defined a suitable photochromic IOL wherein the photochromic agents are so sensitive that even inside the eye, they can be activated by the UV light rays entering through the cornea.

SUMMARY OF THE INVENTION

The present invention relates to a photochromic IOL that, once implanted in the eye, will change into its colored state after being exposed to UV light rays and will become colorless when the UV light rays are absent. The IOL can be used after a cataract patient undergoes cataract removal surgery. The IOL can also be used as a phakic (meaning that the human natural crystalline lens remains in the eye) refractive lens for the correction of myopia, hyperopia, or astigmatism, or any other refractive vision impairment. The IOL can be located in the anterior chamber or posterior chamber of the eye. It can also be an intracorneal lens. In a broad sense, the photochromic agent used in the present invention can be any photochromic agent with an absorption in the visible light region. However, absorption in the blue light region (400-475 nm wavelength) is preferred since blue light absorption may provide additional protection for the retina to reduce the risk for progression of age-related macular degeneration.

Specifically, the present invention relates to a foldable intraocular lens, the optic body of which is made from a crosslinked polymeric composition comprising:
(a) at least one monomer;
(b) a crosslinker;
(c) a UV absorber; and
(d) a photochromic agent;
said intraocular lens having a glass transition temperature of about 37° C. or lower, and said photochromic agent having its maximum absorption peak in the wavelength range of from about 400 to about 500 nm (preferably from about 400 to about 475 nm) in its excited state.

The present invention also relates to methods for forming the photochromic IOL. The photochromic agent can be a simple molecule or a functionalized photochromic molecule. In the latter case, the functional group can be further reacted to form additional chemical bonds with themselves or/and with a polymer network to further stabilize the presence of a photochromic chromophore so that there will be minimal leaching from the IOL. This class of polymers is expected to be very biocompatible and IOLs prepared therefrom perform well in vivo.

Thus, in its method aspect the present invention relates to a method for the preparation of the lenses described herein, comprising the steps of:
(a) blending a photochromic agent and a UV absorber into a pre-polymer composition;
(b) transferring the mixture prepared in step (a) into a mold; and
(c) heating the mold to form said intraocular lens from the mold.

The present invention also encompasses a method for preparation of a foldable intraocular lens, as defined herein, comprising the steps of:
(a) providing an intraocular lens without the photochromic agent;
(b) soaking the finished lens from step (a) in a photochromic agent solution at an elevated temperature so that said lens is slightly swollen to allow photochromic molecules to penetrate into the polymer network; and
(c) drying the soaked lens prepared in step (b) to remove all the solvent.

DETAILED DESCRIPTION OF THE INVENTION

The object of the present invention is to provide an IOL with a sensitive photochromic agent, which will change to the colored state once the patient is in a strong light environment, such as outdoors on a sunny day. Unlike photochromic spectacles or a photochromic contact lens, both of which will be in direct contact with the UV light rays under sunny conditions, the UV light rays have to penetrate through the human cornea layer in order to activate the IOL's photochromic agent. Therefore, the photochromic agents used in the present invention should have a high sensitivity for changing color so that they can respond to the UV light rays received inside the eye. Examples of photochromic agents which may be used in the present invention include triarylmethanes, stilbenes, azastilbenes, nitrones, fulgides, spiropyrans, naphthopyrans, and spiro-oxazines. Examples include 1',3'-dihydro-1',3',3'-trimethyl-6-nitrospiro[2H-1-benzopyran-2,2'-(2H)-indole], a spiropyran, and 1,3-dihydro-1,3,3-trimethyl-spiro[2H-indole-2,3'-[3H]phenanthr[9,10-b](1,4)oxazine], a spiro-oxazine. The photochromic agent is used at a level which is effective to achieve the desired color change sensitivity; preferably it is present at from about 0.01 to about 0.4 wt. % of the optic body of the lens. These amounts are comparable to the levels the dyes would be included in an eyeglasses lens. This is surprising since the eyeglasses lens is exposed to direct sunlight, while the IOL is not, being inside the eye and behind the cornea.

The present invention also includes suitable manufacturing methods for the production of photochromic IOLs. Photochromic agents can be mixed with the monomer mixture or pre-polymer gel and then the mixture is transferred into a suitable mold for curing directly or indirectly into an IOL. Alternatively, finished IOLs can be soaked in a solution of photochromic agent in a suitable solvent that expands the IOL polymer to allow photochromic molecules to penetrate at a molecular level throughout the IOL polymer network. The solvent can be removed by slowly drying the lens in an oven at an elevated temperature.

Examples of polymers which can be used in the manufacture of the lenses of the present invention include those disclosed in U.S. Pat. No. 6,271,281, Liao et al., issued Aug. 7, 2001; U.S. Pat. No. 6,432,137, Nanushyan et al., issued Aug. 13, 2002; U.S. Pat. No. 6,780,899, Liao et al., issued Aug. 24, 2004; U.S. Pat. No. 6,679,605, Zhou et al., issued Jan. 20, 2004; and U.S. Pat. No. 5,444,106, Zhou et al., issued Aug. 22, 1995, all incorporated herein by reference. These examples are from the silicone and acrylic families of polymers. Examples of other useful hydrophobic polymers include polyolefins, such as styrene butadiene and styrene isoprene copolymers having flexible, elastic polymer networks.

In one preferred exemplary embodiment of the present invention, photochromic agents are mixed with a pre-polymer composition at a molecular level and then the mixture is cured into an IOL, either directly in a mold or indirectly by lathing or a combination of both. Any of the conventional IOL designs, i.e., three-piece lens design, one-piece lens design, or full-sized lens design, may be used. Examples 1 and 2 (see below) of the present application illustrate that the pre-mixing method can be successfully used for the preparation of a photochromic IOL. In a simulated physiological condition, the IOL prepared from Example 1 or Example 2 is placed inside a fresh cadaver eye (less than 36 hours since enucleation). Once the cornea of the cadaver eye is exposed to UV light rays, the IOL inside the eye changes into the respective colored state. The IOL from Example 1 develops a slight red color, and the IOL from Example 2 becomes yellow in color.

In this pre-mixing method, the pre-polymer composition preferably includes, but is not limited to, silicone fluids, hydrophobic acrylic monomers or pre-polymer gels, and hydrophilic acrylic monomers or pre-polymer gels. Generally, the pre-polymer composition contains a UV absorber in addition to the photochromic agent. The inclusion of the UV absorber not only provides the IOL with sufficient UV protection, but also further stabilizes the photochromic agent so that the photochromic property can be assured for lifetime usage. Photochromic agents used in the first method can be a simple photochromic molecule, such as a naphthopyran or spiro-oxazine, or a substituted photochromic molecule wherein the substitute group contains one or more functional groups, such as acrylic or alkenyl suitable for free radical polymerization. Where the functionalized agent is used, the photochromic molecule will be chemically bonded with the polymer backbone. Functionalized photochromic agents have been described in U.S. Pat. No. 5,166,345, Akashi et al., issued Nov. 24, 1992, incorporated herein by reference.

In another exemplary embodiment of the present invention, finished IOLs are impregnated in a photochromic agent solution at appropriate conditions to allow sufficient photochromic molecules to penetrate throughout the optic body of the IOL, and are then dried at an elevated temperature. An appropriate organic solvent is preferably used for hydrophobic acrylic or silicone IOLs to allow the IOLs to swell slightly so that the photochromic molecules can be distributed at a molecular level throughout the polymer networks. Examples 3 and 4 (see below) disclose a detailed experimental procedure for the soaking method. IOLs prepared from Example 2 and Example 3 have the same substrate polymer and the same photochromic agent but differ in the method of introducing the photochromic agent into the IOLs. They are found to behave in a similar fashion in the following test. Three groups of IOLs are placed on a sheet of white paper and are exposed to direct sunlight: (a) IOLs without photochromic agent (the control lens); (b) IOLs from Example 2; (c) IOLs from Example 3. It is observed that IOLs from both Example 2 and Example 3 become yellow with a similar color intensity in less than one minute while the control IOLs are colorless. When the three groups of IOLs are moved into an indoor environment, IOLs from Example 2 and Example 3 become colorless in about 1 minute. In this indoor environment, there is no difference in visual appearance among these three groups of IOLs.

In this soaking method, the finished IOL is preferably a soft foldable hydrophobic IOL, such as a silicone and hydrophobic acrylic foldable IOL. As in the pre-mixing method, the photochromic agent can be a simple photochromic molecule or a functionalized photochromic structure. In the latter case, the functional groups can be optionally polymerized to form a second polymer network in the existing lens polymer network (interpenetrating polymer network or IPN). This IPN can further stabilize the presence of the photochromic dye in the IOL.

The lenses of the present invention are foldable, thereby providing most effective insertion into the eye (i.e., requiring the smallest incision). In order to achieve this property, the lenses are made from a polymeric material having a glass transition temperature of about 37° C. (i.e., body temperature) or lower.

EXAMPLE 1

Mixing Photochromic Agent with Pre-polymer Gels Containing a UV Absorber

A mixture of 13 grams of stearylmethacrylate, 7 grams of laurylacrylate, 0.2 grams of 2-[3-(2H-benzotriazol-2-yl)-4-hydroxyphenyl]ethyl methacrylate, 50 milligrams of benzoyl peroxide, 60 µl ethylene glycol dimethacrylate, and 21 milligrams of photochromic dye (PHOTOSOL® 7-106 from PPG Industries, Inc.) is reacted to form a pre-polymer solution. The pre-polymer solution is injected into molds and cured at 90±5° C. for 15±1 hours. After post cure at 135±5.0° C. for 3±1 hours, intraocular lenses are removed from the mold.

One lens thus prepared is completely covered with a fresh (<48 hours) human donor cornea. When the cornea is exposed to UV light, the lens changes into the colored state in less than 1 minute. When the lens is removed from the UV light source, it gradually turns back into its original colorless state.

EXAMPLE 2

Mixing Photochromic Agent with Pre-polymer Gels Containing a UV Absorber

A mixture of 550 g of ethylene glycol phenyl ether acrylate (EGPEA) with 8 g of 2-(4-benzoyl-3-hydroxy-phenoxy) ethyl acrylate (BHP, UV absorber) and 716 mg of azobisisobutyronitrile (AIBN) in a 2-liter round bottom flask is stirred until all solids are dissolved. While stirring, the solution is purged with nitrogen as the temperature is increased to 45±2° C. The viscosity of the solution gradually increases until the viscous pre-polymer condition is achieved. Then, the reaction is quenched by cooling the reaction vessel. A crosslinker, 27.8 g (4.75%) of bisphenol ethoxylate (2 EO/phenol) dimethacrylate, is introduced into the flask. The resulting mixture is stirred vigorously for 2 hours and then degassed under vacuum conditions at room temperature for 5 hours. The pre-polymer solution is filtered through a nominal 8.0 micrometer pore size filter and a 0.65 micrometer pore size filter. The filtered pre-polymer is collected directly into pre-cleaned 10 ml disposable syringes.

10 mg of photochromic dye (PHOTOSOL® 5-3, from PPG Industries, Inc.) is slowly dissolved in 10 g of pre-polymer by stirring in a 25 ml flask. The resulting mixture is transferred into a vial and then is centrifuged for 5 minutes. The mixture is transferred into a standard three-piece design IOL mold and is then cured in an oven with temperature set at 118±5° C. for 13±1 hours. After post cure at 135±5.5° C. for 3±1 hours, IOLs are removed from the molds.

One lens thus prepared is completely covered with a fresh (<48 hours) human donor cornea. When the cornea is exposed to UV light, the lens changes into the colored state in less than 1 minute. When the lens is removed from the UV light source, it gradually turns back into the colorless state.

EXAMPLE 3

Soaking Procedure for Acrylic Lenses in a Photochromic Agent Solution

Finished Matrix hydrophobic acrylic IOLs (Medennium, Inc.) are soaked in a solution of 0.1% PHOTOSOL® 5-3 photochromic dye (PPG Industries, Inc.) in ethanol at 50° C. for 24 hours. The IOLs are then dried at 70° C. for 24 hours. Once the IOL is exposed to direct sunlight rays, it quickly turns a yellow color (<1 minute). When the IOL is moved away from the sunlight rays, its yellow tint gradually disappears in about 1 minute. It is also observed that when the IOL is kept under the tree shade, it becomes slightly yellow compared with control IOLs without photochromic agents.

EXAMPLE 4

Soaking Procedure for Acrylic Lenses in a Photochromic Agent Solution

In a procedure similar to that in Example 3, finished silicone IOLs are used instead of Matrix hydrophobic acrylic IOLs. The absorption of photochromic dye (PHOTOSOL® 5-3, by PPG) into the silicone IOL is successfully demonstrated in a similar fashion as that of Example 3.

EXAMPLE 5

Mixing Photochromic Agent with a Pre-polymer Gel Without a UV Absorber

A mixture of 12 grams of stearylmethacrylate, 5.45 grams of laurylacrylate, 2.5 g of poly (ethylene glycol) dioleate, 50 milligram of benzoyl peroxide, 50 µl ethylene glycol dimethacrylate, and 4 milligram (0.02% by weight) of photochromic dye (Corn Yellow from James Robinson) is reacted while under vigorous stirring to form a pre-polymer gel. The pre-polymer gel is injected into molds and cured at 90±5° C. for 15 f 1 hours. After post cure at 135±5.0° C. for 3±1 hours, intraocular lenses are removed from the mold. IOLs prepared this way appear slightly yellow, suggesting excess amount of photochromic dye was used in the composition. When the slightly yellow IOLs are exposed to the sunlight rays, they become a darker shade of yellow.

The invention claimed is:

1. A foldable intraocular lens, which will change to a colored state when the wearer of the lens is in a strong light environment, the optic body of which is made from a crosslinked polymeric composition comprising:
    (a) at least one monomer;
    (b) a crosslinker;
    (c) a UV absorber; and
    (d) a photochromic agent;
said intraocular lens having a glass transition temperature of about 37° C. or lower, and being activated when exposed to UV light; and said photochromic agent having its maximum absorption peak in the wavelength range of about 400-500 nm in its excited state.

2. The foldable intraocular lens of claim 1 wherein said lens is a replacement lens for cataract patients.

3. The foldable intraocular lens of claim 2 wherein said lens has a structure selected from the group consisting of:
    (a) a three-piece lens design;
    (b) a one-piece lens design; and
    (c) a full-sized lens design.

4. The foldable intraocular lens of claim 1 wherein said lens is a phakic refractive lens structurally adapted for positioning either in the anterior chamber, in the posterior chamber, or within the cornea.

5. The foldable intraocular lens of claim 1 wherein, in said optic body, the at least one monomer and crosslinker form a crosslinked polymeric material selected from the group consisting of hydrophobic acrylic polymers, silicones, hydrogels, collagen-containing polymers, and mixtures thereof.

6. The foldable intraocular lens of claim 1 wherein said photochromic agent is present at from about 0.01% to 0.4% (by wt.) of the optic body.

7. The foldable intraocular lens of claim 6 wherein said photochromic agent includes a functional group which is chemically bonded into the polymer network of the optic body.

8. The foldable intraocular lens of claim 7 wherein said functional group is an acrylic structure.

9. The foldable intraocular lens of claim 7 wherein said functional group is an alkenyl structure.

10. The foldable intraocular lens of claim 6 wherein said photochromic agent contains a simple photochromic chromophore.

11. The foldable intraocular lens of claim 1 wherein said photochromic agent is present in an amount sufficient to be activated by the amount of light entering the eye.

12. The foldable intraocular lens of claim 1 wherein said crosslinked polymeric composition comprises only one monomer.

13. The foldable intraocular lens of claim 1 wherein said crosslinked polymeric composition comprises two or more monomers.

14. The foldable intraocular lens of claim 1 which additionally comprises an effective amount of a UV absorber.

15. The foldable intraocular lens of claim 14 wherein said UV absorber is present at about 1% or less of the optic body.

16. The foldable intraocular lens of claim 1 wherein the photochromic agent is uniformly dispersed in the optic body.

17. The foldable intraocular lens of claim 16 wherein said photochromic agent includes a functional group which is chemically bonded into the polymer network of the optic body.

18. The foldable intraocular lens of claim 17 wherein said functional group is an acrylic structure.

19. The foldable intraocular lens of claim 17 wherein said functional group is an alkenyl structure.

* * * * *